US007943119B2

(12) United States Patent
Tada et al.

(10) Patent No.: US 7,943,119 B2
(45) Date of Patent: May 17, 2011

(54) HAIR COSMETIC COMPOSITION

(75) Inventors: Michiko Tada, Tokyo (JP); Keiko Ishii, Tokyo (JP); Shiyo Shichiri, Tokyo (JP); Tamami Iwase, Tokyo (JP)

(73) Assignee: Kao Corporation, Tokyo (JP)

( * ) Notice: Subject to any disclaimer, the term of this patent is extended or adjusted under 35 U.S.C. 154(b) by 488 days.

(21) Appl. No.: 11/213,881

(22) Filed: Aug. 30, 2005

(65) Prior Publication Data

US 2006/0045862 A1 Mar. 2, 2006

(30) Foreign Application Priority Data

Aug. 31, 2004 (JP) ................................ 2004-251381

(51) Int. Cl.
*A61Q 5/12* (2006.01)
*A61K 8/73* (2006.01)

(52) U.S. Cl. ................................ 424/70.12; 424/70.17

(58) Field of Classification Search ............... 424/70.12, 424/70.17
See application file for complete search history.

(56) References Cited

U.S. PATENT DOCUMENTS

| | | | |
|---|---|---|---|
| 5,403,517 A | 4/1995 | Horinishi et al. | |
| 6,890,543 B2 | 5/2005 | Minami et al. | |
| 6,982,076 B2 | 1/2006 | Kaneko et al. | |
| 7,204,977 B2 | 4/2007 | Asai et al. | |
| 2004/0216248 A1* | 11/2004 | Nocker et al. | 8/406 |
| 2005/0002884 A1* | 1/2005 | Jefferson | 424/70.1 |

FOREIGN PATENT DOCUMENTS

| | | |
|---|---|---|
| EP | 0 640 643 A2 | 3/1995 |
| EP | 1 466 581 A1 | 10/2004 |
| JP | 6-172131 | 6/1994 |
| JP | 09-301831 | * 11/1997 |
| JP | 2002-53444 | 2/2002 |
| JP | 2003-55160 | 2/2003 |

OTHER PUBLICATIONS

Patent Abstracts of Japan, JP 07-258040, Oct. 9, 1995.
Derwent Publications, AN 1995-011727, XP-002356742, JP 06-298625, Oct. 25, 1994.
Derwent Publications, AN 2004-450193, XP-002356743, JP 2004-189727, Jun. 10, 2004.
Derwent Publications, AN 1998-059057, XP-002356744, JP 09-301831, Nov. 25, 1997.
Patent Abstracts of Japan, JP 05-112423, May 7, 1993.

* cited by examiner

*Primary Examiner* — Gollamudi S Kishore
*Assistant Examiner* — Nannette Holloman
(74) *Attorney, Agent, or Firm* — Oblon, Spivak, McClelland, Maier & Neustadt, L.L.P.

(57) ABSTRACT

Provided are a leave-on hair cosmetic composition, containing the following components (A), (B) and (C):

(A) an organic dicarboxylic acid or salt thereof, (B) an organic solvent selected from aromatic alcohols, N-alkylpyrrolidones, alkylene carbonates, polypropylene glycols having a number average molecular weight of from 100 to 1000, lactones and cyclic ketones, and (C) an organopolysiloxane having an organopolysiloxane segment and a poly(N-acylalkyleneimine) segment having a recurring unit represented by the following formula (1):

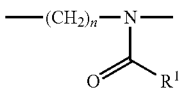

(1)

(wherein, $R^1$: H, $C_{1-22}$ alkyl, cycloalkyl, aralkyl or aryl, and n: 2 or 3), wherein the latter segment has been bonded to at least one silicon atom of the former segment via a hetero-atom-containing alkylene group; having the organopolysiloxane segment and the poly(N-acylalkyleneimine)segment at a weight ratio of from 98/2 to 40/60; and having a weight average molecular weight of from 50,000 to 500,000; and a hair treating method with the composition.

The hair cosmetic composition of the invention can essentially improve the hair quality, give excellent luster, manageability, setting property to the hair, and also give excellent flexible hair feel and elasticity.

8 Claims, No Drawings

HAIR COSMETIC COMPOSITION

FIELD OF THE INVENTION

The present invention relates to a leave-on hair cosmetic composition such as a hair conditioning agent or hair styling agent, which contains an organic acid and a silicone polymer.

BACKGROUND OF THE INVENTION

In recent years, it has been known that owing to the influence by hair coloring or blow drying, cuticles on the hair surface peel off or the hair becomes porous by the efflux of lipids from the inside of the hair and as a result, problems such as excessive dryness, resistance to finger combing, difficulty in styling and loss of luster occur.

Leave-on hair cosmetic compositions mainly used now include emulsion type products such as hair cream containing wax, higher alcohol and surfactant to provide the hair with manageability and protect the hair from excessive dryness; and gel type products containing a film forming polymer (set polymer). Such hair cosmetic compositions can temporarily solve the problems such as poor manageability and excessive dryness by adhering an oil or fat or polymer to the hair surface, but cannot fundamentally improve the hair luster or manageability.

In order to improve the hair quality, compositions that contain a specific organic acid and organic solvent to improve hair quality by acting on the inside of the hair are known (refer to, for example, JP-A-2004-189727, JP-A-1994-172131, and JP-A-1994-298625).

Although these technologies disclosed in the above documents are excellent in effects of improving hair qualities such as luster and manageability, some problems such as less flexibility of the hair, stickiness after application, and heavy hair feel after drying are still remain, when used as a leave-on hair cosmetic composition. In order to solve the problems, conventional silicones are added as a touch improver. The addition of silicone improves hair feel, but disturbs hair quality improving effects (luster, manageability and the like) by addition of the organic acid and organic solvent.

SUMMARY OF THE INVENTION

In the present invention, there is thus provided a leave-on hair cosmetic composition, which contains the following components (A), (B) and (C):

(A) an organic dicarboxylic acid or salt thereof, (B) an organic solvent selected from aromatic alcohols, N-alkylpyrrolidones, alkylene carbonates, polypropylene glycols having a number average molecular weight of from 100 to 1000, lactones and cyclic ketones, and (C) an organopolysiloxane having an organopolysiloxane segment and a poly(N-acylalkyleneimine) segment having a recurring unit represented by the following formula (1):

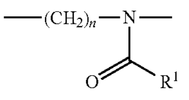

(1)

(wherein, $R^1$ represents a hydrogen atom, a $C_{1-22}$ alkyl group, a cycloalkyl group, an aralkyl group or an aryl group, and n stands for 2 or 0.3); the poly(N-acylalkyleneimine) segment has been bonded to at least one silicon atom of the organopolysiloxane segment via a hetero-atom-containing alkylene group; having the organopolysiloxane segment and the poly(N-acylalkyleneimine)segment at a weight ratio of from 98/2 to 40/60; and having a weight average molecular weight of from 50,000 to 500,000.

DETAILED DESCRIPTION OF THE INVENTION

The present invention relates to a leave-on hair cosmetic composition such as hair styling agent and hair conditioning agent that provide improved hair feel (suppleness, smoothness, and the like) and the hair quality improving effects (improvement in luster, manageability and the like) after drying without disturbance of addition of an organic acid and an organic solvent.

The present inventors have found that the above-described desire can be satisfied by using a specific silicone derivative in combination with an organic dicarboxylic acid and a specific organic solvent.

The hair cosmetic composition of the present invention contributes to essential quality improvement of the hair, and can provide excellent luster, manageability and setting property to the hair, and at the same time, can impart the hair with excellent flexible touch and elasticity. More specifically, the hair cosmetic composition of the present invention is excellent in styling properties both setting property just after hairstyle and set retention under high humidity, can provide stickiness-free and smoothness to the hair both during and after drying used the composition, and can provide suppleness and smooth touch to the hair without stiffness peculiar to the use of a polymer after drying.

The hair cosmetic composition of the present invention is useful as a leave-on hair cosmetic composition for hair setting such as hair styling agent and hair conditioning agent. Frequent use of the composition also provides to the hair improvement of luster, manageability and setting property gradually.

The organic dicarboxylic acid to be used as Component (A) has preferably from 2 to 8 carbon atoms and specific examples include malonic acid, succinic acid, glutaric acid, adipic acid, maleic acid, fumaric acid, phthalic acid, oxalic acid, malic acid, and tartaric acid. Of these, those having at least 3 carbon atoms, including hydroxydicarboxylic acids such as malic acid and tartaric acid, and malonic acid and succinic acid are preferred. Malic acid is more preferred.

Examples of the salts of these organic dicarboxylic acids include salts with an alkali metal, alkaline earth metal, ammonia and organic amine compound.

As Component (A), these compounds may be used in combination of two or more. The content of Component (A) in the hair cosmetic composition of the invention is preferably from 0.1 to 30 wt. %, more preferably from 0.5 to 20 wt. %, even more preferably from 0.5 to 10 wt. % in view of internal hair-quality improving effects (pore repairing effects, and the like), set retention effects and manageability.

The organic solvent to be used as Component (B) of the invention is selected from the following (b1) to (b5).

(b1) Aromatic alcohols represented by the formula (2):

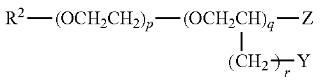

(2)

(wherein, $R^2$ represents a group $R^3$-Ph-$R^4$— ($R^3$: a hydrogen atom, a methyl group or a methoxy group, $R^4$: a bond or a saturated or unsaturated divalent $C_{1-3}$ hydrocarbon group, Ph: a paraphenylene group), Y and Z each represents a hydrogen atom or a hydroxy group, and p, q and r each stands for an integer of from 0 to 5, with the proviso that at p=q=0, Z represents a hydroxy group and $R^2$ does not represent a group $R^3$-Ph-).

(b-2) N-alkylpyrrolidones or N-alkenylpyrrolidones having a nitrogen atom to which a $C_{1-18}$ alkyl or alkenyl group has been bonded.

(b-3) $C_{2-4}$ Alkylene carbonates.

(b-4) Polypropylene glycols having a number average molecular weight of from 100 to 1000.

(b-5) Lactones or cyclic ketones represented by any one of the formulas (3), (4) and (5):

(3)

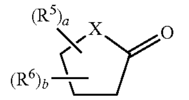

(4)

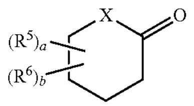

(5)

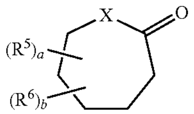

(wherein, X represents a methylene group or an oxygen atom, $R^5$ and $R^6$ each represents a substituent selected from linear, branched or cyclic alkyl groups, hydroxy group, sulfonic group, phosphoric group, carboxy group, phenyl group, sulfoalkyl groups, phosphoalkyl groups and carboxyalkyl groups with the proviso that $R^5$ and $R^6$ do not represent the same group simultaneously, and a and b each stands for 0 or 1).

Of the organic solvents serving as Component (B), examples of (b1) include benzyl alcohol, cinnamyl alcohol, phenethyl alcohol, p-anisyl alcohol, p-methylbenzyl alcohol, phenoxyethanol, and 2-benzyloxyethanol; those of (b2) include N-methylpyrrolidone, N-octylpyrrolidone and N-laurylpyrrolidone; and those of (b3) include ethylene carbonate and propylene carbonate. As the polypropylene glycol (b4) having a number average molecular weight of from 100 to 1000, those having a number average molecular weight of from 100 to 500, particularly from 2 to 5 are preferred. In (b5), $R^5$ and $R^6$ in the formulas (3) to (5) are each preferably a linear or branched $C_{1-6}$ alkyl group such as methyl, ethyl, propyl, isopropyl, or butyl, and preferably substituted at the γ-position in the case of γ-lactone and at the δ-position in the case of δ-lactone (i.e. methylene adjacent to the hetero oxygen atom in both cases). In order to enhance the water solubility of the compounds (3) to (5), $R^5$ or $R^6$ preferably represents an acidic group such as sulfonic group, phosphoric group or carboxy group, or an alkyl group having the above-group as a substituent. In (b5), examples of the lactone include γ-butyrolactone, γ-caprolactone, γ-valerolactone, δ-valerolactone, δ-caprolactone and δ-heptanolactone. Of these, γ-lactone, preferably γ-butyrolactone and γ-caprolactone are preferred in view of the stability of the lactone. Examples of the cyclic ketone as (b5) include cyclopentanone, cyclohexanone, cycloheptanone and 4-methylcycloheptanone.

Examples of the more preferred Component (B) include benzyl alcohol, benzyloxyethanol, propylene carbonate and propylene glycol (number average molecular weight of from 300 to 500, preferably 400).

Component (B) to be used in the invention is preferably a liquid at 25° C. and has a ClogP of from −2 to 3, more preferably from −1 to 2 in view of penetration promotion. The term "ClogP" as used herein means a measure indicating the partition of a substance between an octanol phase and an aqueous phase. It is a calculated value of an octanol-water partition coefficient (logp) as defined by the below-described equation and its examples is described in *Chemical Reviews,* 71(6), 1971.

$$\log P=\log([\text{Substance}]_{octanol}/[\text{Substance}]_{water})$$

wherein, $[\text{Substance}]_{octanol}$ means a mole concentration of a substance in a 1-octanol phase, while $[\text{Substance}]_{water}$ means a mole concentration of the substance in an aqueous phase.

Exemplary of the ClogP of Component (B) is benzyl alcohol (1.1), 2-benzyloxyethanol (1.2), 2-phenylethanol (1.2), 1-phenoxy-2-propanol (1.1), polypropylene glycol 400 (0.9), propylene carbonate (−0.41), and γ-butyrolactone (−0.64).

The composition may contain two or more compounds of Component (B) in combination. The content of component (B) in the hair cosmetic composition of the invention is preferably from 0.1 to 40 wt. %, more preferably from 0.5 to 10 wt. %, even more preferably from 1 to 5 wt. % in view of its feeling upon use, hair luster and hair quality improving effects (improvement of elasticity, moisture resistance, and the like).

A weight ratio of the organic dicarboxylic acid or salt thereof as Component (A) to the organic solvent as Component (B) preferably, (A):(B) ranges from 10:1 to 1:7, more preferably from 4:1 to 1:3 in view of effectively produce internal hair-quality improving (pore repairing) effects, set retention improving effects and manageability improving effects.

Component (C) is an organopolysiloxane in which a poly (N-acylalkyleneimine) segment having a recurring unit represented by the following formula (1):

(1)

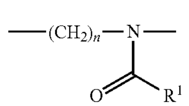

(wherein $R^1$ represents a hydrogen atom, a $C_{1-22}$ alkyl group, a cycloalkyl group, an aralkyl group or an aryl group, and n stands for 2 or 3) has been bonded to at least one silicon atom of an organopolysiloxane segment via a hetero-atom-containing alkylene group. $R^1$ is preferably a methyl or ethyl group.

The organopolysiloxane as Component (C) has a organopolysiloxane segment and a poly(N-acylalkyleneimine) segment at a weight ratio of from 98/2 to 40/60, preferably from 94/6 to 60/40 and it has a weight average molecular weight of from 50,000 to 500,000, preferably from 100,000 to 300,000.

Examples of the hetero-atom-containing alkylene group via which the organopolysiloxane segment and poly(N-acylalkyleneimine) is bonded include $C_{2-20}$ alkylene groups having 1 to 3 nitrogen atoms, oxygen atoms and/or sulfur atoms. Specific examples include:

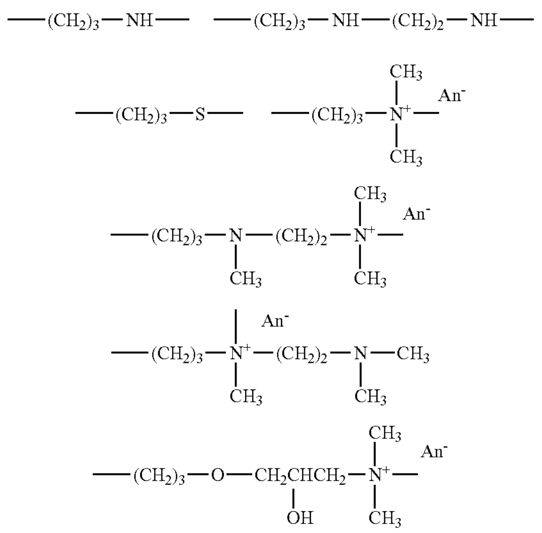

(wherein, $An^-$ represents an anion). Among them, $C_{2-5}$ alkylene groups having a nitrogen atom are preferred. As $R^1$, the cycloalkyl group is, for example, that having 3 to 6 carbon atoms, the aralkyl group is, for example, a phenylalkyl or naphthyl alkyl group, and the aryl group is, for example, a phenyl, naphthyl, or alkyl-substituted phenyl group.

The organopolysiloxane as Component (C) can be prepared in a known process. For example, the component (C) is prepared in accordance with the method as described in JP-A-1995-133352 by reacting an organopolysiloxane represented by the following formula (6):

(6)

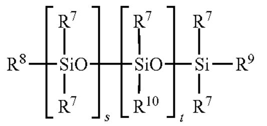

(wherein, $R^7$s may be the same or different and each represents a $C_{1-22}$ alkyl group or a phenyl group, $R^8$ and $R^9$ each represents the same group as $R^7$ or a group represented by any one of the following formulas:

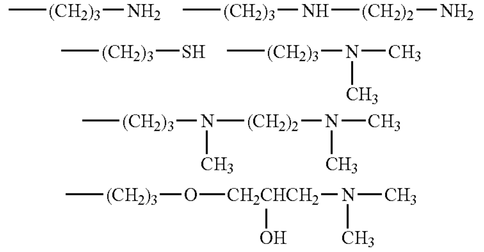

$R^{10}$ represents the above-described formula, s stands for an integer of from 100 to 4000 and t stands for an integer of from 1 to 300) with a terminal-reactive poly(N-acylalkyleneimine) available by the open-ring polymerization of a cyclic iminoether represented by the following formula (7):

(7)

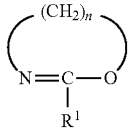

(wherein, $R^1$ and n have the same meanings as described above).

The ring-opening polymerization of the cyclic iminoether (7) can be carried out in accordance with the method as described, for example, in *Liebigs Ann. Chem.*, p996-p1009 (1974). The polymerization initiator herein is compounds having strong electrophilic reactivity, for example, methyl, ethyl, 3-propenyl or benzyl esters of strong acids such as benzenesulfonic acid, p-toluenesulfonic acid, trifluoromethanesulfonic acid, trifluoroacetic acid, or sulfuric acid. Of these, alkyl toluenesulfonates, dialkyl sulfates and alkyl trifluoromethanesulfonates are preferred. For example, poly(N-acylethyleneimine) (compound of formula (1), in which n=2) can be obtained by 2-substituted-2-oxazoline as the cyclic iminoether (7). When 2-substituted-dihydro-2-oxazine is used, poly(N-acylpropyleneimine) (compound of formula (1), in which n=3) can be obtained. The molecular weight of the molecular chain of the poly(N-acylalkyleneimine) is preferably from 150 to 50,000, more preferably from 500 to 10,000.

The above-described poly(N-acylalkyleneimine) chain and a silicone chain can be bonded utilizing a variety of reactions, which include an ester forming reaction based on the condensation between a carboxy group and a hydroxy group; an amide forming reaction-based on the condensation of a carboxy group and an amino group; a secondary, tertiary or quaternary ammonium forming reaction between an alkyl halide group and a primary, secondary or tertiary amino group; addition reaction of an Si—H group to a vinyl group; and a β-hydroxyamine forming reaction using an epoxy group and an amino group. As disclosed in JP-A-1990-276824, JP-A-1992-85334, JP-A-1992-85335, JP-A-1992-96933 or the like, a method in which a terminal reactive poly(N-acylalkyleneimine) available by the cationic ring-opening polymerization of a cyclic iminoether is reacted with an organopolysiloxane represented by the formula (6), i.e., a modified organopolysiloxane having, on the side chain thereof, the above-described substituent is convenient and effective.

The reaction between the amino-containing organopolysiloxane and the reactive terminal of poly(N-acylalkyleneimine) obtained by the cationic polymerization of the cyclic iminoether is carried out, for example, in the following manner. The initiator is dissolved in a polar solvent such as acetonitrile, valeronitrile, dimethylformamide, dimethylacetamide, chloroform, methylene chloride, ethylene chloride, ethyl acetate or methyl acetate or mixture thereof if necessary, followed by temperature elevation to 40 to 150° C., preferably 60 to 100° C. Then, the cyclic iminoether represented by the above formula (7) is charged at a time, or is added dropwise thereto if the reaction is vigorous for polymerization. The polymerization can be monitored by determined the residual amount of the cyclic iminoether, which is a monomer, by an analyzing apparatus such as gas chromatography. Even after the cyclic iminoether is consumed and the polymerization is completed, the active radical at the growing terminal maintains its reactivity. Without isolation of the resulting polymer, the polymer solution is then reacted with an organopolysiloxane having an amino group from 5 to 100° C., preferably from 20 to 60° C. The mixing ratio of the polymer solution and organopolysiloxane can be selected as desired, from 0.1 to 1.3 molar equivalents of poly(N-acylalkyleneimine) with 1 mole of the amino group of organopolysiloxane is preferred. As a result, a block copolymer or graft polymer that a poly(N-acylalkyleneimine) segment is bonded to the polydimethylsiloxane can be obtained.

Examples of the organopolysiloxane as Component (C) include poly(N-formylethyleneimine)organosiloxane, poly (N-acetylethyleneimine)organosiloxane, and poly(N-propionylethyleneimine)organosiloxane.

The Component (C) can be used two or more in combination and the content in the hair cosmetic composition of the present invention is preferably from 0.1 to 10 wt. %, more preferably from 0.5 to 5 wt. % from the standpoint of improvement of the hair feel without reducing the hair quality improving effect brought by Components (A) and (B).

The hair cosmetic composition of the present invention may contain an α-hydroxymonocarboxylic acid as Component (D). Nonlimiting examples of the α-hydroxymonocarboxylic acid include glycolic acid, lactic acid, α-oxybutyric acid and glyceric acid, of which lactic acid being preferred.

The content of the α-hydroxymonocarboxylic acid as Component (D) is preferably from 0.01 to 30 wt. %, more preferably from 0.1 to 20 wt. %, more preferably from 0.5 to 10 wt. % in the hair cosmetic composition of the present invention from the standpoints of improvement in the hair luster, flexibility and manageability and prevention of excessive dryness.

The hair cosmetic composition herein may further contain ethanol. It is believed that ethanol contributes to the solubilization or stable dispersion of Component (B). It is also believed that ethanol contributes to the solubilization of Components (A) and (C), whereby the penetration of them into the hair is promoted. The content of ethanol in the hair cosmetic composition of the invention is preferably from 0.01 to 50 wt. %, more preferably from 1 to 20 wt. %. An weight ratio preferably of ethanol to component (B), ethanol:Component (B) ranges from 40:1 to 2:1, more preferably from 20:1 to 3:1 from the viewpoint of penetration promotion of Components (A) and (B) into the hair.

The hair cosmetic composition of the invention may further contain a set polymer in view of improvement of hair styling property, regulation of viscosity, stability, improvement of adhesion during application to the hair, improvement of hair feel and early manifestation of hair quality improving effects. Nonlimiting examples of the polymer include polyvinylpyrrolidone polymer compounds such as polyvinylpyrrolidone, vinylpyrrolidone/vinyl acetate copolymer, vinylpyrrolidone/vinyl acetate/vinyl propionate ternary copolymer, vinylpyrrolidone/alkylaminoacrylate (quaternized chloride) copolymer, vinylpyrrolidone/acrylate/(meth) acrylic acid copolymer, and vinylpyrrolidone/alkylaminoacrylate/vinylcaprolactam copolymer; acidic vinyl ether polymer compounds such as methyl vinyl ether/maleic anhydride alkyl half ester copolymer; acidic polyvinyl acetate polymer compounds such as vinyl acetate/crotonic acid copolymer, vinyl acetate/crotonic acid/vinyl neodecanoate copolymer, and vinyl acetate/crotonic acid/vinyl propionate copolymer, acidic acrylic polymer compounds such as (meth) acrylic acid/(meth)acrylate copolymer, and acrylic acid/alkyl acrylate/alkylacrylamide copolymer; amphoteric acrylic polymer compounds such as N-methacryloylethyl-N,N-dimethylammonium•α-N-methylcarboxybetaine/butyl methacrylate copolymer, and hydroxypropyl acrylate/butylaminoethyl methacrylate/acrylic octylamide copolymer; basic acrylic polymer compounds such as acrylamide•acrylate quaternary copolymer; cellulose derivatives such as cationic cellulose derivative; and chitin•chitosan derivatives such as hydroxypropyl chitosan, carboxymethyl chitin, and carboxymethyl chitosan.

These set polymers may be used either singly or in combination of two or more. Their content in the hair cosmetic composition of the invention is preferably from 0.1 to 10 wt. %, more preferably from 0.5 to 5 wt. %.

Oil can be also added to improve the hair manageability after drying. Nonlimiting examples include hydrocarbons such as squalene, squalane, liquid isoparaffin, light liquid isoparaffin, heavy liquid isoparaffin, α-olefin oligomer, liquid paraffin and cycloparaffin; glycerides such as castor oil, cacao oil, mink oil, avocado oil and olive oil; waxes such as bees wax, sperm wax, lanolin, microcrystalline wax, ceresin wax and carnauba wax; higher alcohols such as cetyl alcohol, oleyl alcohol, stearyl alcohol, isostearyl alcohol and 2-octyldodecanol; esters such as octyldodecyl myristate, hexyl laurate, cetyl lactate, propylene glycol monostearate, oleyl oleate, hexadecyl 2-ethylhexanoate, isononyl isononanoate and tridecyl isononanoate; higher fatty acids such as capric acid, lauric acid, myristic acid, palmitic acid, stearic acid, behenic acid, oleic acid, coconut oil fatty acid, isostearic acid and isopalmitic acid; and other oils such as isostearyl glyceryl ether and polyoxypropylene butyl ether. Of these, branched hydrocarbons including squalene, squalane, liquid isoparaffin, light liquid isoparaffin, heavy liquid isoparaffin, α-olefin oligomer are preferred.

The content of the oil in the hair cosmetic composition of the invention is preferably from 0.05 to 20 wt. %, more preferably from 0.1 to 10 wt. %, even more preferably from 0.5 to 5 wt. % in view of good manageability and stickiness-free feel.

In the hair cosmetic composition of the invention, a surfactant may be incorporated in order to improve the stability including solubilization of a solvent contained or dispersibility of the composition and to improve the hair feel. The surfactant herein can include cationic surfactant, nonionic surfactant, amphoteric surfactant and anionic surfactant.

Examples of the cationic surfactant include quaternary ammonium salts represented by the following formula (8):

(8)

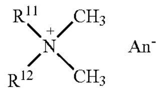

(wherein $R^{11}$ and $R^{12}$ each independently represents a hydrogen atom, a $C_{1-28}$ alkyl group or a benzyl group, with the proviso that they do not simultaneously represent a hydrogen atom, a benzyl group or a $C_{1-3}$ lower alkyl group, and $An^-$ represents an anion).

Either one of $R^{11}$ and $R^{12}$ preferably represents an alkyl group having from 16 to 24 carbon atoms, more preferably 22 carbon atoms, even more preferably a linear alkyl group, while the other one represents a lower $C_{1-3}$ alkyl group, preferably a methyl group. Examples of the anion $An^-$ include halide ions such as chloride ions and bromide ions, and organic anions such as ethyl sulfate ions and methyl carbonate ions. Of these, halide ions, suitably chloride ions are preferred.

As the cationic surfactant, mono(long chain alkyl) quaternary ammonium salts are preferred. Specific examples include cetyltrimethylammonium chloride, stearyltrimethylammonium chloride, arachyltrimethylammonium chloride and behenyltrimethylammonium chloride. Of these, stearyltrimethylammonium chloride and behenyltrimethylammonium chloride are more preferred.

Examples of the nonionic surfactant include polyoxyalkylene $C_{6-30}$ alkyl ethers, polyoxyalkylene $C_{6-30}$ alkenyl ethers, higher fatty acid sucrose esters, polyglycerin fatty acid esters, higher fatty acid mono- or di-ethanolamides, polyoxyethylene hydrogenated castor oils, polyoxyethylene sorbitan fatty acid esters, polyoxyethylene sorbitol fatty acid esters, $C_{6-30}$ alkyl saccharide surfactants, $C_{6-30}$ alkylamine oxides, and $C_{6-30}$ alkylamide amine oxides. Of these, polyoxyalkylene $C_{6-30}$ alkyl ethers and polyoxyethylene hydrogenated castor oils are preferred, with polyoxyethylene $C_{6-30}$ alkyl ethers being more preferred.

As the amphoteric surfactant, imidazoline, carbobetaine, amidobetaine, sulfobetaine, hydroxysulfobetaine, and amidosulfobetaine can be used.

Nonlimiting examples of the anionic surfactant include alkylbenzene sulfonates, alkyl or alkenyl ether sulfates, alkyl or alkenyl sulfates, olefin sulfonates, alkane sulfonates, saturated or unsaturated fatty acid salts, alkyl or alkenyl ether carboxylates, α-sulfone fatty acid salts, N-acylamino acid surfactants, mono- or di-phosphate ester surfactants and sulfosuccinates. Examples of the counterion as the anionic residue of the above-described surfactants include alkali metal ions such as sodium ion and potassium ion; alkaline earth metal ions such as calcium ion and magnesium ion, ammonium ions, alkanolamines having 1 to 3 alkanol groups with 2 or 3 carbon atoms (such as monoethanolamine, diethanolamine, triethanolamine and triisopropanolamine). Examples of the counterion as the cationic residue include halide ions such as chloride ions, bromide ions and iodide ions, methosulfate ions and saccharinate ions.

Of these, cationic surfactants are preferred in view of hair feel. These surfactants may be used either singly or in combination of two or more. The content of the surfactant(s) in the hair cosmetic composition of the invention is preferably from 0.01 to 10 wt. %, more preferably from 0.05 to 3 wt. % in view of stabilization that includes solubilization of solvents and emulsification of oils, of the composition.

The hair cosmetic composition of the invention may further contain a polyhydric alcohol. It is believed that the polyhydric alcohol contributes to solubilization and stable dispersion of Component (B). In addition, the enhancement of the hair quality improving effect may be accelerated by the synergistic action between the polyhydric alcohol and Component (B). Nonlimiting examples of the polyhydric alcohol include ethylene glycol, glycerin, sorbitol, propylene glycol, 1,3-butyleneglycol and dipropylene glycol. Of these, glycerin is preferred. These polyhydric alcohols may be used either singly or in combination of two or more. Its content in the hair cosmetic composition of the invention is preferably from 0.1 to 10 wt. %, more preferably from 0.5 to 5 wt. %.

The hair cosmetic composition of the invention may further contain, as needed, components employed for ordinary hair cosmetic compositions depending on their purpose of use. Examples of such components include antidandruffs, vitamin preparations, bactericides, anti-inflammatories, chelating agents, humectants such as sorbitol and panthenol, coloring agents such as dyes and pigments, viscosity regulators such as hydroxyethyl cellulose, methyl cellulose, polyethylene glycol and clay mineral, pH regulators such as organic acids other than Component (A), sodium hydroxide and potassium hydroxide, plant extracts, pearling agents, perfumes, colorants, ultraviolet absorbers, antioxidants, and the other components as described in ENCYCLOPEDIA OF SHAMPOO INGREDIENTS (MICELLE PRESS).

The hair cosmetic composition of the invention is adjusted to have a pH of from 2.5 to 4.5 at 25° C. when diluted to 20 times the weight with water, from the standpoints of promoting penetration and adsorption of Components (A) and (B) to the hair and at the same time, providing luster, flexibility, manageability and suppleness to the hair. Preferably, the pH value is from 2.5 to 4, more preferably from 3 to 4.

The form of the hair cosmetic composition of the invention can be selected from liquid, gel, paste, cream and wax as needed, but that in the form of a solution using, as a solvent, water or a lower alcohol is preferred, among which water is preferred.

The hair cosmetic composition of the invention is preferably used as a hair styling agent or hair conditioning agent. It can be provided, for example, as a pump spray, aerosol spray, pump foam, aerosol foam, gel or lotion.

By blowing or heating the hair after application of the hair cosmetic composition of the invention, penetration of Components (A) and (B) into the hair can be accelerated. The hair can be heated by a hair iron, drier, heater or rod-shaped hair iron. The heating temperature is preferably 60° C. or greater, more preferably 70° C. or greater.

In daily life, frequent use of the hair cosmetic composition of the present invention can provide improvement of luster, manageability and setting property.

EXAMPLES

The pH in the below-described examples is a value at 25° C. when the composition is diluted to 20 times the weight with water.

Example 1

Hair cosmetic compositions as shown in Table 2 were prepared and their "setting property", "strength/body improving effect", "manageability", "hair feel" and "luster" were evaluated. The results are also shown in Table 2.

(Evaluation Method)

Evaluation of "Setting Property"

1) Hair Bundle to be Evaluated

A hair bundle of 10 cm in length, 1.5 cm in width and 1 g in weight was prepared by the hair of a Japanese female not subjected to chemical treatment such as permanent waving and hair coloring. The hair bundle was bleached (by "Ravenus Color Appeal Inazuma Bleach"; product of Kao) twice and then the hair bundle was provided for the evaluation of setting property.

2) Treatment of the Hair Bundle

Pre-Shampoo Evaluation (Treatment 7 Times)

After the hair bundle to be evaluated was shampooed (with "Ravenus Designing Shampoo", product of Kao) and towel dried, 0.1 g of the invention product or comparative product (which will hereinafter be called "treatment agent") was applied uniformly to the hair bundle. The hair bundle was then dried for 10 minutes with hot air of 70° C. This treatment was repeated six times in total. After shampooing, towel drying and application of the treatment agent in a similar manner, the hair bundle was curled around a rod having a diameter of 4 cm and dried for 10 minutes with hot air of 70° C.

Post-Shampoo Evaluation

The internal hair-quality improving effect was studied by evaluating the set retention after the treatment agent was washed away from the hair surface. After completion of the pre-shampoo evaluation, each hair bundle was shampooed and towel dried. Without application of the treatment agent to the hair, the hair bundle was curled around a rod having a diameter of 4 cm and dried for 10 minutes with hot air of 70° C.

3) Procedures and Criteria of Evaluation

The curled bundle was removed from the rod and a comb (ring comb) was caused to run through the bundle 20 times to disentangle it. The bundle then was suspended in a thermo-hygrostatic box (25° C. and 98% RH) to determine the set retention power. Described specifically, the length of the hair bundle suspended (distance from the bundled position to the end of the hair) was measured. A length just after suspension was defined as 100% set retention and an initial length (10 cm) before curling was defined as 0% set retention. A relative value (%) of the length of the hair bundle after 30 minutes, that is, a percent set retention after 30 minutes was determined in accordance with the following equation:

$$\text{Set retention (\%)} = \frac{\text{(initial length of the hair bundle)} - \text{(length of the hair bundle after 30 minutes)}}{\text{(initial length of the hair bundle)} - \text{(length of the hair bundle just after curling)}} \times 100$$

Evaluation of "Strength/Body Improving Effect", "Manageability", "Hair Feel (Smoothness, Moistness, Softness, Stiffness, Stickiness)" and "Luster"

1) Hair Bundle to be Evaluated

A hair bundle of 25 cm in length and 6 g in weight was prepared by using the hair of a Japanese female not subjected to chemical treatment such as permanent waving and hair coloring. The hair bundle was bleached (with "Ravenus Color Appeal Inazuma Bleach"; product of Kao) twice and the resulting hair bundle was provided for the evaluation.

2) Treatment of the Hair Bundle

Pre-Shampoo Evaluation

After the hair bundle to be evaluated was shampooed (with "Ravenus Designing Shampoo", product of Kao) and towel dried, 0.6 g of the treatment agent was applied uniformly to the hair bundle. The treated hair bundle was dried for 10 minutes with hot air of 70° C. while combing by a ring comb through the hair bundle. This treatment was repeated seven times in total.

Post-Shampoo Evaluation

In order to evaluate the internal hair-quality improving effect, the hair bundle after completion of the pre-shampoo evaluation was shampooed and towel-dried, and then dried for 10 minutes with hot air of 70° C. while running a ring comb through the hair bundle.

Evaluation During Drying

With regards to "stickiness", the hair feel during drying was also evaluated.

3) Evaluation Criteria

Organoleptic evaluation by a panel of 5 experts was performed in accordance with the criteria shown in Table 1 and an average of the scores is shown in Table 2.

TABLE 1

| (Strength/body improving effects) | (Manageability) |
|---|---|
| 4: Obvious improvement in strength/body | 4: Excellent manageability |
| 3: Improvement in strength/body | 3: Some manageability |
| 2: Some improvement in strength/body | 2: Difficult to evaluate |
| 1: Only slight improvement in strength/body | 1: A little inferior in manageability |
| 0: No improvement in strength/body | 0: Lack of manageability |
| **(Hair feel: smoothness)** | **(Hair feel: moist feel)** |
| 4: Very Smooth | 4: Very moist |
| 3: Smooth | 3: Moist |
| 2: Difficult to evaluate | 2: Difficult to evaluate |
| 1: Slightly smooth | 1: Slightly moist |
| 0: Not smooth | 0: Not moist |
| **(Hair feel: softness)** | **(Hair feel: stiffness)** |
| 4: Very soft | 4: Not stiff |
| 3: Soft | 3: Slightly stiff |
| 2: Difficult to evaluate | 2: Difficult to evaluate |
| 1: Slightly soft | 1: Stiff |
| 0: Not soft | 0: Very stiff |
| **(Hair feel: stickiness)** | **(Luster)** |
| 4: Not sticky | 4: Marked improvement in luster |
| 3: Slightly sticky | 3: Improvement in luster |
| 2: Difficult to evaluate | 2: Difficult to evaluate |
| 1: Sticky | 1: No improvement in luster |
| 0: Very sticky | 0: Loss of luster |

TABLE 2

| | | Example products | | | Comparative products | | | | |
|---|---|---|---|---|---|---|---|---|---|
| | | 1 | 2 | 3 | 1 | 2 | 3 | 4 | 5 |
| Composition (wt. %) | Malic acid | 2.5 | 2.5 | 8.0 | 2.5 | 2.5 | 2.5 | — | — |
| | Lactic acid | — | — | 8.0 | — | — | — | — | — |
| | Glycolic acid | — | — | — | — | — | 4.5 | — | — |
| | Citric acid | — | — | — | — | — | — | — | 6.0 |
| | 2-benzyloxyethanol | 2.5 | — | 5.0 | 2.5 | 2.5 | 2.5 | 2.5 | 2.5 |
| | Benzyl alcohol | — | 5.0 | — | — | — | — | — | — |
| | Oxazoline-modified organopolysiloxane *1 | 0.5 | 4.0 | 1.0 | — | — | — | 0.5 | 0.5 |
| | Dimethicone *2 | — | — | — | — | 0.5 | — | — | — |
| | Polyether-modified silicone *3 | — | — | — | — | — | 0.5 | — | — |
| | Stearyltrimethylammonium chloride | 1.0 | 1.0 | 1.0 | 1.0 | 1.0 | 1.0 | 1.0 | 1.0 |
| | Glycerin | 1.0 | 1.0 | 1.0 | 1.0 | 1.0 | 1.0 | 1.0 | 1.0 |
| | Ethanol | 10.0 | 10.0 | 10.0 | 10.0 | 10.0 | 10.0 | 10.0 | 10.0 |
| | Water | Balance | Balance | Balance | Balance | Balance | Balance | Balance | Balance |
| | Sodium hydroxide (pH regulator) | q.s. | q.s. | q.s. | q.s. | q.s. | q.s. | q.s. | q.s. |

TABLE 2-continued

| | | | Example products | | | Comparative products | | | | |
|---|---|---|---|---|---|---|---|---|---|---|
| | | | 1 | 2 | 3 | 1 | 2 | 3 | 4 | 5 |
| pH (at 25° C., when diluted to 20 times the weight with water) | | | 3.7 | 3.0 | 3.7 | 3.7 | 3.7 | 3.7 | 3.7 | 3.7 |
| Evaluation | During drying | Stickiness | 2.8 | 3.2 | 3.0 | 1.0 | 1.6 | 1.6 | 1.2 | 0.6 |
| | Before shampoo | Setting property | 90 | 80 | 100 | 90 | 40 | 40 | 40 | 60 |
| | | Strength/body improving effects | 3.2 | 3.0 | 3.6 | 3.0 | 1.6 | 1.6 | 1.6 | 2.4 |
| | | Manageability | 3.2 | 3.0 | 4.0 | 2.0 | 1.6 | 1.6 | 1.6 | 2.4 |
| | | Smoothness | 3.6 | 4.0 | 3.6 | 0.6 | 2.4 | 1.0 | 1.6 | 2.4 |
| | | Moist feel | 2.6 | 3.6 | 3.2 | 1.6 | 2.0 | 1.2 | 1.6 | 2.0 |
| | | Softness | 2.4 | 3.6 | 3.6 | 1.2 | 1.6 | 1.2 | 3.0 | 2.4 |
| | | Stiffness | 3.0 | 3.6 | 3.6 | 0.6 | 2.8 | 1.2 | 2.8 | 2.4 |
| | | Stickiness | 3.0 | 3.6 | 3.6 | 2.0 | 3.0 | 1.6 | 2.8 | 3.0 |
| | | Luster | 3.6 | 3.6 | 3.6 | 3.6 | 1.8 | 1.2 | 2.0 | 2.0 |
| | After shampoo | Setting property | 80 | 75 | 90 | 80 | 25 | 25 | 10 | 50 |
| | | Strength/body improving effect | 3.2 | 3.6 | 3.6 | 2.6 | 1.2 | 1.2 | 1.0 | 2.0 |
| | | Manageability | 2.8 | 3.6 | 3.6 | 1.0 | 0.6 | 0.6 | 0.4 | 1.4 |

*1 Elastomer OS-88 (Kao Corporation)
*2 Silicone KM-9716 (Shin-etsu Chemical)
*3 Silicone KF-353A (Shin-etsu Chemical)

From the above-described results, it has been confirmed that unlike hair cosmetic compositions which are available by the conventional technology which cannot solve the problems such as stiffness and stickiness, the compositions according to the present invention can attain good setting property, strength/body improving effects, manageability and hair feel improving effects. Even after the removal of the components attached to the surface of the hair by shampooing, the above-described effects last. In addition, the hair quality improving effects such as elimination of pores inside of the hair are confirmed.

Example 2

Set retention was evaluated in a similar manner to Example 1 when a hair bundle similar to that used in Example 1 was treated once, three times or seven times with the hair cosmetic composition (Example Product 4) described below was evaluated. The results are shown in Table 3.

Pre-Shampoo Evaluation (Single Treatment)

The hair bundle to be evaluated was shampooed (with Ravenus Designing Shampoo, product of Kao Corporation) and towel dried. Then, 0.1 g of the agent (Example Product 4) was uniformly applied to the hair bundle. The hair bundle was wound around a rod having a diameter of 4 cm and (1) dried for 30 minutes with air of room temperature (25° C.) (drying at room temperature), (2) dried for 10 minutes with hot air of 70° C. (blow drying), and (3) wound around a curling hair iron (4 cm in diameter) heated to 120° C. (styled with a curling hair iron).

(Three-Times or Seven-Times Treatment)

After the hair bundle to be evaluated was shampooed and towel dried, 0.1 of the agent was applied uniformly to it, followed by drying with hot air of 70° C. for 10 minutes. This treatment was repeated twice or six times in total and then, the resulting hair bundle was treated in a similar manner to the above-described “single treatment” (three kinds, that is, drying at room temperature, blow drying, hair styling with a curling hair iron).

Post-Shampoo Evaluation

After completion of the pre-shampoo evaluation, each hair bundle was shampooed and towel dried. Without application of the agent to the hair, the hair bundle was wound round a rod having a diameter of 4 cm and dried for 10 minutes with hot air of 70° C.

Formulation of Hair Cosmetic Composition (Example Product 4)

| | (wt. %) |
|---|---|
| Malic acid | 1.25 |
| Lactic acid | 1.25 |
| 2-Benzyloxyethanol | 1.25 |
| Oxazoline-modified organopolysiloxane (“Elastomer OS-96”, product of Kao Corporation) | 0.5 |
| Stearyltrimethylammonium chloride | 1.0 |
| Glycerin | 1.0 |
| Ethanol | 10.0 |
| Isopropylmethylphenol | 0.7 |
| Water | Balance |
| Sodium hydroxide (pH regulator) | to adjust pH to 4.0 |

TABLE 3

| | | | Drying method of agent-applied hair | | |
|---|---|---|---|---|---|
| | | | Drying at room temperature | Blow drying | Hair styling with a curling hair iron |
| Setting property | Single treatment | After shampoo | 40 | 60 | 85 |
| | | Before shampoo | 20 | 50 | 70 |
| | Three-times treatment | After shampoo | 70 | 80 | 90 |
| | | Before shampoo | 60 | 70 | 80 |

TABLE 3-continued

| | | Drying method of agent-applied hair | | |
|---|---|---|---|---|
| | | Drying at room temperature | Blow drying | Hair styling with a curling hair iron |
| Seven-times treatment | After shampoo | 80 | 90 | 90 |
| | Before shampoo | 80 | 90 | 90 |

Example 3

A pump spray having the below-described composition was prepared.

| | (wt. %) |
|---|---|
| Malic acid | 2.50 |
| Lactic acid | 2.50 |
| Oxazoline-modified organopolysiloxane ("Elastomer OS-88", product of Kao Corporation) | 0.10 |
| Stearyltrimethylammonium chloride | 0.25 |
| Glycerin | 1.00 |
| 2-Benzyloxyethanol | 2.50 |
| Ethanol | 4.50 |
| Perfume | 0.02 |
| Water | Balance |
| Sodium hydroxide (pH regulator) | to adjust pH to 3.7 |

Example 4

A pump mist having the below-described composition was prepared.

| | (wt. %) |
|---|---|
| Malic acid | 4.00 |
| Lactic acid | 1.00 |
| Oxazoline-modified organopolysiloxane ("Elastomer OS-88", product of Kao Corporation) | 5.00 |
| 2-Benzyloxyethanol | 2.50 |
| Polyvinylpyrrolidone | 3.00 |
| Ethanol | 10.00 |
| Perfume | 0.05 |
| Water | Balance |
| Sodium hydroxide (pH regulator) | to adjust pH to 3.7 |

Example 5

A hair gel having the below-described composition was prepared.

| | (wt. %) |
|---|---|
| Malic acid | 2.50 |
| Lactic acid | 2.50 |
| Oxazoline-modified organopolysiloxane ("Elastomer OS-88", product of Kao Corporation) | 1.00 |
| Glycerin | 2.00 |
| Stearyltrimethylammonium chloride | 0.25 |
| 2-Benzyloxyethanol | 2.50 |
| Hydroxyethyl cellulose | 2.00 |
| Ethanol | 10.00 |
| Perfume | 0.05 |
| Water | Balance |
| Sodium hydroxide (pH regulator) | to adjust pH to 3.7 |

Example 6

A hair lotion having the below-described composition was prepared.

| | (wt. %) |
|---|---|
| Malic acid | 1.00 |
| Lactic acid | 4.00 |
| Oxazoline-modified organopolysiloxane ("Elastomer OS-88", product of Kao Corporation) | 1.00 |
| stearyltrimethylammonium chloride | 0.25 |
| Glycerin | 1.00 |
| 2-Benzyloxyethanol | 2.50 |
| Ethanol | 10.00 |
| Perfume | 0.02 |
| Water | Balance |
| Sodium hydroxide (pH regulator) | to adjust pH to 3.7 |

Example 7

An aerosol spray was obtained by mixing the below-described mixed stock and, as a propellant, a nitrogen gas at a ratio of 99.5/0.5.

| | (wt. %) |
|---|---|
| Malic acid | 2.50 |
| Lactic acid | 2.50 |
| Oxazoline-modified organopolysiloxane ("Elastomer OS-88", product of Kao Corporation) | 1.00 |
| Stearyltrimethylammonium chloride | 0.25 |
| Glycerin | 1.00 |
| 2-Benzyloxyethanol | 2.50 |
| Ethanol | 4.50 |
| Perfume | 0.02 |
| Water | Balance |
| Sodium hydroxide (pH regulator) | to adjust pH to 3.7 |

Example 8

A pump foam having the below-described composition was prepared.

| | (wt. %) |
|---|---|
| Malic acid | 2.50 |
| Lactic acid | 2.50 |
| Oxazoline-modified organopolysiloxane ("Elastomer OS-88", product of Kao Corporation) | 1.00 |
| Polyoxyethylene lauryl ether (16E.O.) | 1.00 |
| Stearyltrimethylammonium chloride | 0.25 |
| Glycerin | 1.00 |
| 2-Benzyloxyethanol | 2.50 |

-continued

| | (wt. %) |
|---|---|
| Ethanol | 4.50 |
| Perfume | 0.02 |
| Water | Balance |
| Sodium hydroxide (pH regulator) | to adjust pH to 3.7 |

Example 9

An aerosol foam was obtained by mixing the below-described mixed stock and, as a propellant, LPG (0.44 MPa) at a ratio of 93/7.

| | (wt. %) |
|---|---|
| Malic acid | 4.00 |
| Lactic acid | 1.00 |
| Oxazoline-modified organopolysiloxane ("Elastomer OS-88", product of Kao Corporation) | 1.00 |
| Polyoxyethylene lauryl ether (16E.O.) | 1.00 |
| Stearyltrimethylammonium chloride | 0.25 |
| Glycerin | 1.00 |
| 2-Benzyloxyethanol | 2.50 |
| Ethanol | 4.50 |
| Perfume | 0.02 |
| Water | Balance |
| Sodium hydroxide (pH regulator) | to adjust pH to 3.7 |

What is claimed is:

1. A leave-on hair cosmetic composition, which comprises the following components (A), (B) and (C):

(A) from 0.1 to 10 wt. % of malic acid or a salt thereof, (B) from 0.1 to 5 wt. % of at least one organic solvent selected from the group consisting of benzyl alcohol and 2-benzyloxyethanol, and (C) from 0.5 to 5 wt. % of at least one organopolysiloxane having an organopolysiloxane segment and a poly(N-acylalkyleneimine) segment having a recurring unit represented by the following formula (1):

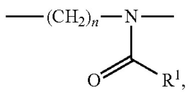

(1)

wherein R1 represents an ethyl group, and n is 2, wherein the poly(N-acylalkyleneimine) segment has been bonded to at least one silicon atom of the organopolysiloxane segment via a hetero-atom-containing alkylene group, wherein the hetero-atom-containing alkylene group is $—(CH_2)_3—NH—$, and further comprises from 1 to 20 wt. % of ethanol, wherein a pH of the leave-on hair cosmetic composition when diluted to 20 times the weight with water is from 3 to 4.5 at 25° C.

2. The hair cosmetic composition according to claim 1, further comprising at least one α-hydroxymonocarboxylic acid or salt thereof.

3. A hair quality improving method, comprising applying the leave-on hair cosmetic composition as claimed in claim 1 or 2 to the hair and then heating.

4. The hair cosmetic composition of claim 2, comprising from 0.01 to 30 wt. % of the at least one α-hydroxymonocarboxylic acid or salt thereof.

5. The hair cosmetic composition of claim 2, wherein at least one α-hydroxymonocarboxylic acid is lactic acid.

6. The hair quality improving method of claim 3, wherein a temperature of the heating is at least 70° C.

7. A hair quality improving method, comprising applying at least daily the leave-on hair cosmetic composition as claimed in claim 1 or 2 to the hair and then heating.

8. The hair quality improving method of claim 7, wherein a temperature of the heating is at least 70° C.

* * * * *